United States Patent [19]

Lübbers et al.

[11] Patent Number: 5,368,027

[45] Date of Patent: Nov. 29, 1994

[54] SENSOR ARRANGEMENT FOR DIRECT OR INDIRECT OPTICAL DETERMINATION OF PHYSICAL OR CHEMICAL PROPERTIES

[75] Inventors: Dietrich W. Lübbers, Dortmund, Germany; Hellfried Karpf, Graz, Austria

[73] Assignee: AVL Medical Instruments AG, Schaffhausen, Switzerland

[21] Appl. No.: 43,802

[22] Filed: Apr. 7, 1993

[30] Foreign Application Priority Data

Apr. 23, 1992 [AT] Austria ............................ 838/92

[51] Int. Cl.$^5$ .............................................. A61B 5/00
[52] U.S. Cl. ........................... 128/633; 128/637; 128/654; 128/636; 128/667; 128/736
[58] Field of Search .................. 128/633–635, 128/637, 664–667, 653.4, 654, 736, 636

[56] References Cited

U.S. PATENT DOCUMENTS

| | | | |
|---|---|---|---|
| 3,341,417 | 9/1967 | Sinaiko | 128/654 X |
| 4,136,683 | 1/1979 | Gordon | 128/654 |
| 4,577,636 | 3/1986 | Spears | 128/654 |
| 4,582,061 | 4/1986 | Fry | 128/654 X |
| 5,057,431 | 10/1991 | Lübbers et al. | |
| 5,092,331 | 3/1992 | Nakamura et al. | 128/665 X |

Primary Examiner—Angela D. Sykes
Attorney, Agent, or Firm—Watson, Cole, Grindle & Watson

[57] ABSTRACT

In a sensor arrangement for direct or indirect optical determination of physical or chemical parameters, in human and animal bodies, the sensor arrangement including an indicator cell which is permeable to the chemical substance or physical quantity to be measured and which contains one or more indicators, a radiation source supplying the excitation radiation for the indicator, and a detector for detection of the response radiation emitted by the indicator, the indicator cell is configured as a capsule which may be introduced into body cavities, such as mouth, nose, stomach, intestine, blood vessels, bronchial tubes, urinary bladder, or which may be implanted in the tissue, and the material used for this capsule is transparent to excitation radiation and to the response radiation emitted by the indicator in the range of wavelengths between 600 and 1,300 nm, and the material of the capsule, or rather, its outer layer, is bio-compatible.

15 Claims, 2 Drawing Sheets

SENSOR ARRANGEMENT FOR DIRECT OR INDIRECT OPTICAL DETERMINATION OF PHYSICAL OR CHEMICAL PROPERTIES

BACKGROUND OF THE INVENTION

The invention relates to a sensor arrangement for direct or indirect optical determination of physical or chemical parameters, comprising an indicator cell, which is permeable to the chemical substance or physical quantity to be measured and contains one or more indicators, and further comprising a radiation source supplying the excitation radiation for the indicator, and a detector for detection of the response radiation emitted by the indicator, in which contact between the radiation source and the indicator, or the indicator and the detector is exclusively established via the excitation radiation and the response radiation.

DESCRIPTION OF THE PRIOR ART

A sensor arrangement of the above type is described in DE-A1 30 01 669, for example. To prevent the indicator from being washed out of the indicator cell, it is covalently bonded to a membrane sealing the indicator cell. In this way the permeability of the membrane to the substances to be measured is improved without an increased release of the indicator medium.

As is well known, human and animal tissue, in particular the skin, is characterized by its relatively good transparency to optical radiation in the red and infrared range of 600 to 1,300 nm. As there are substances produced by the body itself with characteristic absorption spectra in this range, these substances may be detected inside the body by non-invasive methods, i.e., through a kind of optical window.

Such windows are used, for example, to determine photometrically the degree of oxygen saturation of intravascular haemoglobin. With modern techniques it is possible, for instance, to measure oxygenated and deoxygenated haemoglobin inside the skull of a newborn, thus permitting continuous monitoring of the oxygen supply of the brain. In pulse oxymetry, a method for detecting the arterial oxygen saturation of haemoglobin, the phenomenon of the optical window also is utilized.

In recent years even substances that are not produced by the body itself have been introduced into the body and measured at the exposed surface of the respective organ (VANDERKOOT et al.: The Journal of Biological Chemistry, Vol. 262, No. 12, pp. 5476–5482, 1987). In the above wave range, for example, the phosphorescence of an oxygen indicator bound to serum albumin is measured inside the blood vessels and the intravascular oxygen concentration at the surface of the brain is determined in this way. Distribution problems in the tissue and reactions of tissue components may result in measurement errors, however. If several vessels are situated one above the other, for instance, it is almost impossible to locate them precisely, as the indicator signal itself is used for localization. Another disadvantage is that only non-toxic indicators may be employed which do not cause any biological reactions.

SUMMARY OF THE INVENTION

It is an object of the invention to propose a sensor arrangement based on the device described above, by means of which physical or chemical parameters in human or animal bodies can be determined more accurately, enabling the measured value to be assigned to its respective measurement site with high regional resolution, and permitting the use of toxic indicators.

In the invention this is achieved by configuring the indicator cell as a capsule which may be introduced into body cavities, such as mouth, nose, stomach, intestine, blood vessels, bronchial tubes, urinary bladder, etc., or is implantable in the tissue, and by providing that the material used for the capsule be transparent to excitation radiation and the response radiation emitted by the indicator in the range of wavelengths between 600 and 1,300 nm, and that the capsule material, or rather, its outer layer be biocompatible. Due to these provisions the measurement site where the physical or chemical parameter is determined is precisely defined, since the indicator is neither diluted nor unpredictably distributed in the tissue. As the indicator medium is enclosed by the capsule and any direct contact between biological tissue and the indicator is thus prevented, the use of toxic or tissue-incompatible indicator media is made possible. If the indicator is supplied in a matrix, the latter must be transparent in the range of 600 to 1,300 nm. The indicator may react to the parameter to be measured either directly, i.e., by changing its optical properties, or indirectly, i.e., via a reaction product or an intermediate reaction. Suitable indicators are luminescence indicators and absorption indicators. Biocompatible in this context means that the material used for the capsule should be biostable and should not cause any major changes or disturbances of the biological processes taking place in the body. The substance to be measured may be concentrated by selective diffusion and solubility, or by carriers in the material of the capsule, which will further increase measuring accuracy.

The capsule may be made of a polymer material transparent in the wave range between 600 and 1,300 nm, or it may be made of glass. In another variant to be discussed in greater detail below, the capsule preferably is made of a dialytic membrane.

It is an additional advantage if the capsule can be sterilized by heat, or pressure radiation, without any degrading effects on its functions.

The capsule, which on account of its measuring window in the wave range of 600 to 1,300 nm will be referred to below as a "window optode", may have various shapes depending on its particular use.

For examinations of the gastro-intestinal tract, in particular, a capsule of essentially spherical, lenticular or cylindrical shape with rounded edges could be used, which the patient can swallow without problems. For example, polymer capsules have been produced whose diameter is less than 1 micrometer. In spatial measurements the simultaneous use of several indicators with different optical properties may be preferable, which are contained in a single capsule, or in a number of capsules.

In a further development of the invention the capsules may be configured as string- or tube-like structures, or as thin sheets. By implanting one or several sheet-type window optodes, it will be possible in the instance of muscular-cutaneous transplants, for example, to determine by tissue pH measurement whether the oxygen supply is satisfactory. Another use would be in local pH measurement at the surface of the brain, with the cranium closed, for instance after cerebral surgery. After implantation of the suitable capsules or window optodes, the pH may be monitored from outside without causing the patient undue discomfort. As the implantation wound is closed and no direct connection to an optical fiber is required, the risk of infection is kept to a minimum compared to that caused by invasive measuring methods.

The window optode may be attached by simple surgical methods; for example, the capsules may be fastened on a string or a two-dimensional network. At the end of the measuring process or test period, the capsules may be removed and their measuring function checked.

In a further development of the invention the the capsule is provided with particles permitting its localization, which may be effected by optical means or ultrasonic techniques or X-rays inside the body.

It may be of special advantage, in particular for measurements in reflected light, to provide the capsule with at least one reflecting surface which is adjacent to the indicator or a layer containing the indicator. The indicator inside the capsule may be embedded in a hydrogel layer, for example.

The principle of the window optode may be employed in all measuring processes involving quantities for which suitable indicators are available. In particular, indicator media are to be provided for measuring ionic concentration, partial gas pressure, concentration of enzyme or substrate, ionic strength, pressure, and temperature.

In this context, chemical variables such as pH, ionic concentrations of potassium, calcium, sodium or magnesium, partial pressures of carbon dioxide, oxygen or ammonia, and physical variables such as pressure and temperature should be specially mentioned. Moreover, the determination of substrates such as glucose, lactate, creatinine, etc., is of importance, which is possible with the use of suitable indicators and the sensor arrangement of the invention.

BRIEF DESCRIPTION OF THE DRAWINGS

The invention will be further described with reference to the accompanying drawings, in which FIG. 1 gives a schematical view of a sensor arrangement of the invention.

DETAILED DESCRIPTION OF PREFERRED EMBODIMENTS

Figure 1:
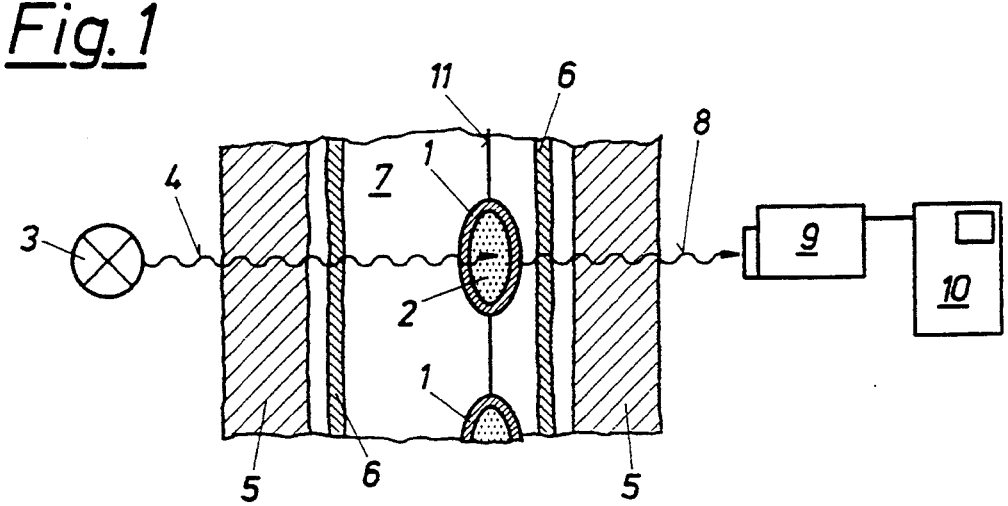

The sensor arrangement presented in FIG. 1 may be used for pH measurement in the stomach of an infant, for example. For this purpose a capsule 1 containing the indicator 2 is introduced into the stomach. The excitation radiation 4 emitted by a radiation source 3 in the wave range of 600 to 1,300 nm penetrates the body tissue 5, the gastric wall 6, the capsule 1 in the gastric lumen 7, and excites the indicator 2. After passing the capsule 1, the gastric wall 6 and the body tissue 5, the response radiation 8 emitted by the indicator 2 arrives at a detector 9, which is connected to an evaluation unit 10. In the example shown in the drawing a hydrogel containing a pH indicator is enclosed within the capsule 1. The material used for the capsule is a dialytic membrane permeable to $H+$ ions, such that a change in the pH value in the stomach will act upon the optical parameters of the indicator, and a change in response radiation can be detected by the detector 9. The capsule 1 may be attached to a string 11, or several capsules 1 may be attached on a string 11, permitting the performance of pH measurements at defined distances. The capsule 1, or rather, the capsule membrane need not be selective to $H+$ ions, if two pH indicators are provided in the capsule and the method described in Sensors and Actuators 4 (1983), 473–479 is used for monitoring the ionic strength sensitivity of ion indicators.

By selecting suitable indicators other ions may be measured, of course, such as potassium, calcium, sodium or magnesium. An absorption or luminescence indicator may be used, whose optical properties are determined by the pH value of its immediate environment. Depending on the respective indicator, the sensor arrangement will be used to measure changes in absorption or luminescence by known methods.

Figure 2:
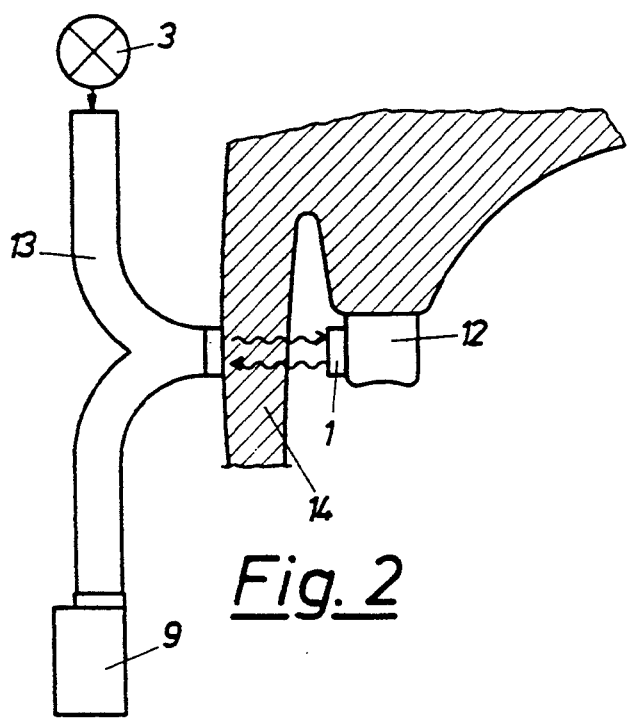
FIG. 2 shows a variant of the sensor arrangement of FIG. 1, FIGS. 3 to 7 show variants of capsules enclosing the indicator, i.e., so-called "window optodes" of the sensor arrangements of FIG. 1 and 2.
Figure 3:
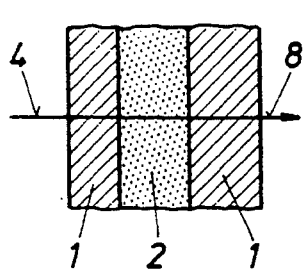
Figure 4:
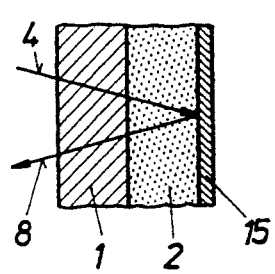
Figure 5:
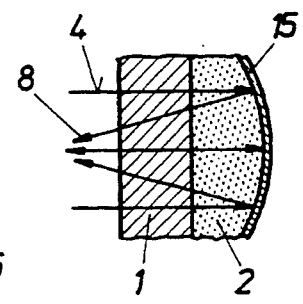

Another example of non-invasive pH measurement in body cavities accessible from outside, with the use of an IR window optode, is shown in FIG. 2. In this instance, the capsule 1 for pH determination in the mouth is attached to a tooth 12, and the excitation and response radiation transmitted by a two-arm optical fiber 13 passes through the cheek 14 in the area of the capsule 1. The optical fiber 13 is placed in such a way as to obtain a maximum signal. Whereas in the arrangement of FIG. 1 passing light is utilized for measuring (cf. detail of capsule shown in FIG. 3), reflected light is used in the arrangement of FIG. 2, a reflecting surface 15 being provided in the capsule, in particular, if absorption indicators are used, which surface 15 is adjacent to the indicator 2 or a layer containing the indicator. Details of such capsules are shown in FIGS. 4 and the reflecting surface 15 being plane in FIG. 4 and concave in FIG. 5. In the arrangement of FIG. 2 the reflecting surface is provided on the side of the capsule 1 next to the tooth 12.

A configuration similar to the one shown in FIG. 2 may be used for measuring the partial pressure of $O_2$ or $CO_2$ in the nose, where a window optode with a suitable indicator is fastened inside the nose, and the excitation radiation may be entered and the response radiation may be carried off by means of a spectacle-like device sitting on the nose. This will permit the patient to move freely and without impediment to his breathing.

Figure 6:
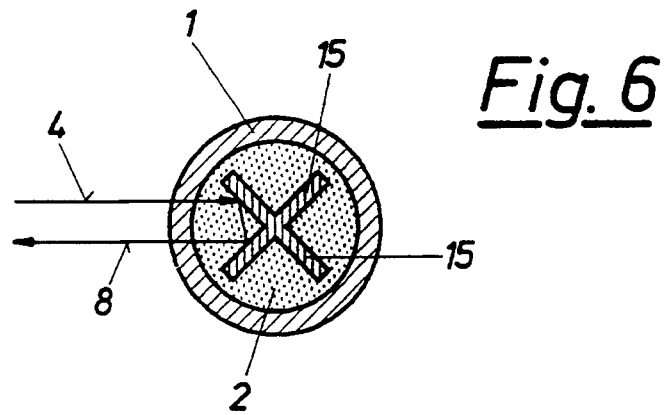

According to FIG. 6 it will be possible to arrange several reflecting surfaces 15 inside the capsule 1 such that the response radiation 8 is reflected parallel to the incident excitation radiation 4.

Figure 7:
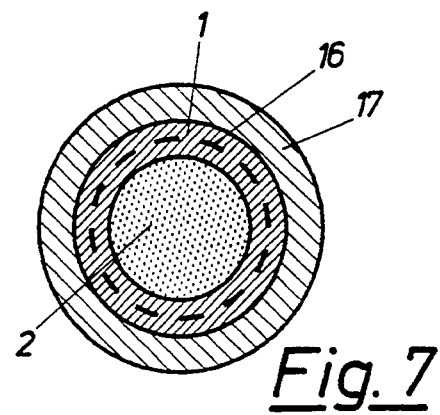

To permit accurate localization of the measuring site in the body, the capsule 1 may be provided with particles 16 in its interior or in its wall, which permit localization by optical or ultrasonic means or with the use of X-rays. The capsule 1 shown in FIG. 7 has such particles 16 in its wall, the capsule itself being surrounded by a biocompatible layer 17.

Figure 8:
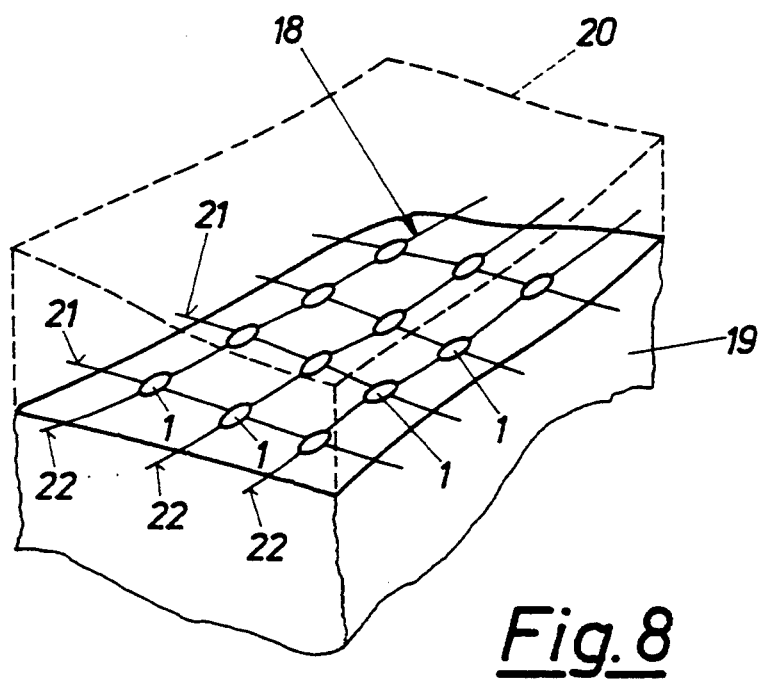
FIG. 8 shows the arrangement of several capsules in a network.

FIG. 8, finally, shows non-invasive pH measurement after implantation of several capsules 1 attached to a two-dimensional network 18. By determining the pH of tissue, for example, this device will tell the user whether the oxygen supply between the tissue 19 and the transplant 20 is satisfactory. The shape of the implanted window optodes may be matched with the structure of the tissue within which the implantation is made; instead of the network 18 a sheet-like optode could be used for smaller areas. If the transverse threads 21 of the network 18 are made of material that is resorbed by the body, suitably shaped capsules may be removed from the tissue by means of the longitudinal threads 22 at the end of the measurement series.

We claim:

1. A sensor arrangement for direct or indirect optical determination of physical or chemical parameters, comprising a radiation source supplying an excitation radiation for at least one indicator, a detector means for detection of a response radiation emitted by said indicator, in which contact between said radiation source and said indicator, and between said indicator and said detector, is exclusively established via said excitation radiation and said response radiation, and an indicator cell which comprises a capsule which is introduceable into body cavities, such as mouth, nose, stomach, intestine, blood vessels, bronchial tubes, urinary bladder, or which is implantable in the tissue, said capsule being permeable to a chemical substance or physical quantity to be measured, and at least one indicator in said capsule, wherein material used for said capsule is transparent to said excitation radiation and to said response radiation in the range of wavelengths between 600 and 1,300 nm, and wherein at least an outer layer of said capsule material is biocompatible.

2. A sensor according to claim 1, wherein said capsule is of essentially one of a spherical, lenticular and cylindrical shape with rounded edges.

3. A sensor arrangement according to claim 2, wherein at least one said capsule is attached on a string.

4. A sensor arrangement according to claim 2, wherein a plurality of said capsules are attached to a two-dimensional network.

5. A sensor arrangement according to claim 1, wherein said capsule is configured as one of a string- and tube-like structure.

6. A sensor arrangement according to claim 1, wherein said capsule is configured as a sheet-like structure.

7. A sensor arrangement according to claim 1, wherein said capsule is sterilizable.

8. A sensor arrangement according to claim 1, wherein said capsule is provided with particles permitting its localization inside the body by one of optical means, ultrasonic techniques, and X-rays.

9. A sensor arrangement according to claim 1, wherein said capsule is provided with at least one reflecting surface which is positioned adjacent to said at least one indicator.

10. A sensor arrangement according to claim 1, wherein said capsule is provided with at least one reflecting surface which is positioned adjacent to a layer containing said indicator.

11. A sensor arrangement according to claim 1, wherein said indicator inside said capsule is embedded in a hydrogel layer.

12. A sensor arrangement according to claim 1, wherein said capsule is made of polymer material transparent in the wave range between 600 and 1,300 nm.

13. A sensor arrangement according to claim 12, wherein said capsule is made of a dialytic membrane.

14. A sensor arrangement according to claim 1, wherein said capsule is made of glass transparent in the wave range between 600 and 1,300 nm.

15. A sensor arrangement according to claim 1, wherein said at least one indicator in said capsule is provided for measuring at least one physical or chemical parameter from a group consisting of ionic concentration, partial gas pressure, concentration of enzyme or substrate, ionic strength, pressure, and temperature.

* * * * *